United States Patent [19]
Gass et al.

[11] Patent Number: 5,583,643
[45] Date of Patent: Dec. 10, 1996

[54] METHODS OF AND APPARATUS FOR MEASUREMENT USING ACOUSTO-OPTIC DEVICES

[75] Inventors: Paul A. Gass, St. Davids; John R. Sambles, Copplestone, both of England

[73] Assignee: British Technology Group Ltd., London, England

[21] Appl. No.: 433,804

[22] Filed: May 3, 1995

Related U.S. Application Data

[63] Continuation of Ser. No. 133,121, Oct. 12, 1993, abandoned.

[30] Foreign Application Priority Data

Apr. 12, 1991 [GB] United Kingdom .................. 9107796

[51] Int. Cl.$^6$ .......................... G01N 21/17; G01N 21/43
[52] U.S. Cl. ........................................ 356/445; 356/432
[58] Field of Search .................................. 356/416, 419, 356/445, 448, 432 T, 432, 447; 350/445

[56] References Cited

U.S. PATENT DOCUMENTS

| | | |
|---|---|---|
| 3,914,055 | 10/1975 | Wolga et al. . |
| 3,994,592 | 11/1976 | Lardon et al. ............................ 356/419 |
| 4,053,236 | 10/1977 | Atwood et al. .......................... 356/419 |
| 4,097,751 | 6/1978 | Egan et al. ................................ 356/447 |
| 4,273,421 | 6/1981 | Gurtler ...................................... 356/432 |
| 4,627,730 | 12/1986 | Jungerman et al. . |
| 4,652,757 | 3/1987 | Carver ....................................... 356/432 |
| 4,741,620 | 5/1988 | Wickramasinghe . |
| 4,804,271 | 2/1989 | Cammann ............................... 356/416 |
| 4,830,504 | 5/1989 | Frohardt et al. ......................... 356/448 |
| 5,023,053 | 6/1991 | Finlan ...................................... 356/445 |
| 5,153,503 | 10/1992 | Yahata .................................. 324/158 D |
| 5,351,127 | 9/1994 | King et al. .............................. 356/445 |

FOREIGN PATENT DOCUMENTS

| | | |
|---|---|---|
| 0250070 | 12/1987 | European Pat. Off. . |
| 0405462 | 1/1991 | European Pat. Off. . |
| 0417551 | 3/1991 | European Pat. Off. . |
| 2146116 | 4/1985 | United Kingdom . |
| 2209603 | 5/1989 | United Kingdom . |
| 2142427 | 1/1995 | United Kingdom . |
| 89009380 | 10/1989 | WIPO . |

OTHER PUBLICATIONS

Applied Optics, vol. 25, No. 18, 15 Sep. 1986, pp. 3014–3017.
H. Chung et al "Simplified Diference Phase Optical Microscope" ehole document.
Applied Optics, vol. 29, No. 31, 1 Nov. 1990, pp. 4694–4704, E. Fontana et al.
"Surface Plasmon Immunoassay" see pp. 4695–4697.
Optics Communications, vol. 59, No. 5 1 Oct. 1986, pp. 361–365 K. Oda et al.
"Instantaneous Observation of Total Refirction Spectra" see pp. 361–363.

Primary Examiner—Richard A. Rosenberger
Attorney, Agent, or Firm—Cushman, Darby & Cushman

[57] ABSTRACT

Optical measuring apparatus including an acousto-optical device (3) which molulates either the angle or the wavelength of a light beam (1) at a frequency determined by a signal generator (15). A detector (13) detects the modulated beam after interrogation of a sample under test; and a lock-in amplifier (14) is connected to the signal generator (15) and to the detector (13) to determine the differential of an optical property of the sample under test.

21 Claims, 6 Drawing Sheets

METHODS OF AND APPARATUS FOR MEASUREMENT USING ACOUSTO-OPTIC DEVICES

This is a continuation of application Ser. No. 08/133,121, filed on Oct. 12, 1993, which was abandoned upon the filing hereof.

FIELD OF THE INVENTION

This invention relates to the use of acousto-optic devices and, in particular, to phase-sensitive optical measurements using such devices.

BACKGROUND OF THE INVENTION

Optical techniques are exploited in a very wide range of measurement technologies. An important factor in any measurement is the sensitivity to small changes in the physical property being measured. Therefore an invention which can enhance the sensitivity of several types of optical measurement has many potential applications.

Acousto-optic devices rely on the interaction of optical and acoustic waves within certain transparent materials. They are extensively used in optical systems to control the intensity, wavelength and beam direction of light. The two types of acousto-optic devices which are used in this invention are acousto-optical deflectors and acousto-optic tunable filters. As their names imply an acousto-optic deflector will electronically control the angle through which a light beam is deflected on traversing the device and an acousto-optic tunable filter will control the wavelength of light transmitted by the device. The important features of these devices are their very fast scan rate and continuous scan range. In both these respects acousto-optic devices are superior to their electromechanical equivalents, although more limited in angle and wavelength scan range.

SUMMARY OF THE INVENTION

According to the present invention optical measuring apparatus for measuring a phase-related optical property of a sample comprises:

an optical source to provide a beam of optical radiation;

a signal generator to provide a modulation signal at a modulation frequency;

an acousto-optical modulator to receive the modulation signal and the beam of optical radiation and to modulate a parameter of the beam at the modulation frequency;

optical means to direct at least a part of the modulated beam so that after incidence on a sample under test as a modulated probe beam it is received by photosensitive means which provides a related modulated electrical sample signal; and phase sensitive signal processing means to receive the modulated electrical sample signal and the modulation signal and to derive therefrom an output signal related to the differential of an optical property of the sample.

Optionally the phase sensitive signal processing means is a lock-in amplifier.

The acousto-optical modulator may be an acousto-optical deflector which modulates the angel of deflection of the optical beam traversing the modulator, or alternatively may be an acousto-optical tunable filter which modulates the wavelength of the optical beam.

Also according to the invention optical measuring apparatus for measuring a phase-related optical property of a sample comprises:

an optical source to provide a beam of optical radiation;

a signal generator, a voltage controlled frequency source and a acousto-optical modulator connected in series so that the modulator modulates the angle of the beam at a frequency determined by the voltage controlled frequency source;

beam splitter to divide the modulated beam into a modulated probe beam and a modulated reference beam, the modulated probe beam interacting with the sample;

first and second photosensitive means to receive the modulated probe beam and the modulated reference beam and to provide respective related electrical signals;

first signal processing means to receive the respective related signals and derive therefrom a ratio signal representing the ration of the modulated probe beam and the modulated reference beam; and phase sensitive second signal processing means to receive the ratio signal and the modulation signal and to derive therefrom an output signal related to the differential of the optical property of the sample.

In a variation, the phase sensitive second signal processing means also supplies the signal to the voltage controlled frequency source as a feedback signal and to micro-computer means.

Also according to the invention, a method of measuring a phase-related optical property of a sample comprises steps of:

providing a beam of optical radiation;

modulating a parameter of a beam at a modulation frequency;

directing at least a part of the modulated beam to a sample under test as a modulated probe beam;

receiving form the sample a beam derived from the modulated probe beam and providing a related electrical sample signal; and deriving from the electrical sample signal a signal at the modulation frequency an output signal related to the differential of an optical property of the sample.

BRIEF DESCRIPTION OF THE DRAWINGS

The invention will now be particularly described with reference to the accompanying drawings in which.

DESCRIPTION OF PREFERRED EMBODIMENTS

Referring to the drawings, an optical measurement system uses an acousto-optic deflector or acousto-optic tunable filter to modulate the angle of incidence or wavelength of the light beam which is being used to probe a sample or sensor element. If the optical properties of the sample are angle (momentum) or wavelength (momentum or energy) dependent then a suitably placed photodetector will receive a modulated signal at the same frequency as the acousto-optic modulation. This signal can be fed to a lock-in amplifier using the acousto-optic modulation frequency as the reference. In principle, only that component of the photodetector signal which is due to the variation of the sample's optical properties will then be amplified. Because the size of the output signal from the amplifier is proportional to the modulation of the photodetector signal it is in fact a direct measurement of the differential of the sample's optical properties with respect to angle or wavelength.

Figure 1:
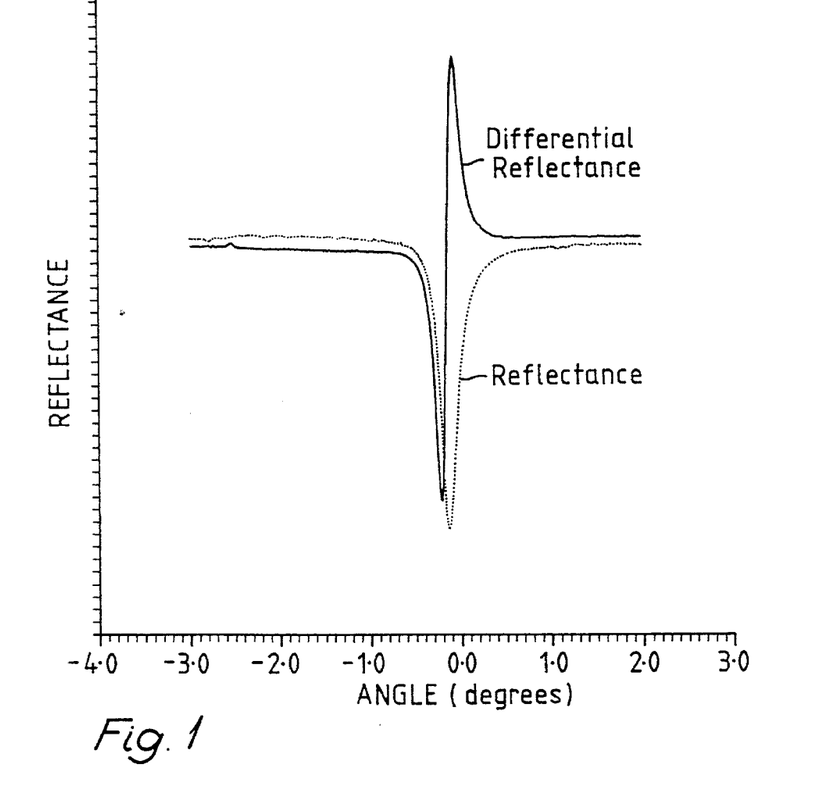
FIG. 1 shows the reflectance of a layer of silver on a fused silica prism.
Figure 2:
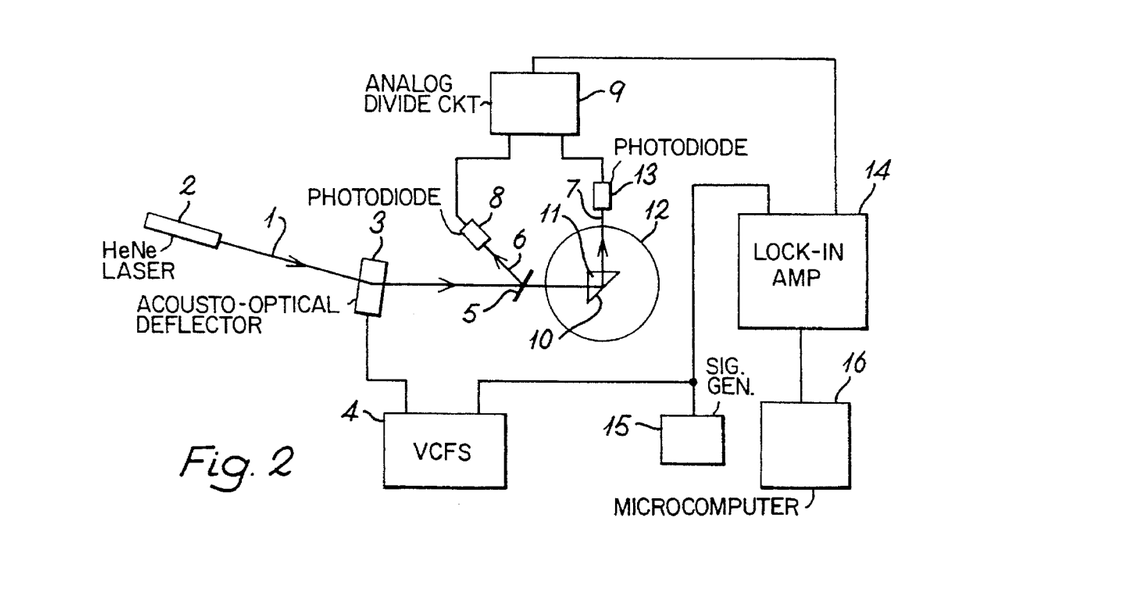
FIG. 2 is a schematic representation of apparatus used for measurement of differential reflectance.

This is illustrated in FIG. 1 where the dotted line shows the reflectance as a function of angle for a silver layer on a fused silica prism. The dip in reflectance is caused by a typical surface plasmon-polariton resonance at the silver air interface. The continuous line shows the differential of this reflectance, (dR/dr), which was directly measured using an acousto-optic deflector to modulate the incident angle as illustrated in FIG. 2. In this, a beam 1 of radiation from a HeNe laser 2 passes to an acousto-optical deflector 3 controlled by a frequency modulated drive signal from a voltage controlled frequency source (VCFS) 4. A partially reflecting mirror 5 splits the radiation into a reference beam 6 and a probe beam 7. The reference beam 6 is detected by a photodiode 8 and passes to one input of an analog divide circuit 9. The probe beam 7 is reflected from a silvered layer on one surface 10 of a prism 11 mounted on a computer controlled rotating stage 12. It then passes to a photodiode 13 which is coupled to the other input of the analog divide circuit 9. A signal representative of the ratio of the signal to reference voltages passes from the divider circuit to an input of a lock in amplifier 14 which is also fed from the signal generator 15 which provides a frequency modulation signal to the VCFS 4. A differential signal passes from the lock-in amplifier 14 to a microcomputer 16.

The importance of measuring the true differential is that it allows the measurement of very weak optical features which would normally be dominated by large, perhaps noisy, background signals. Conventional beam amplitude modulation together with phase sensitive detection will also reduce noise but will not eliminate the effect of large background signals.

Figure 3:
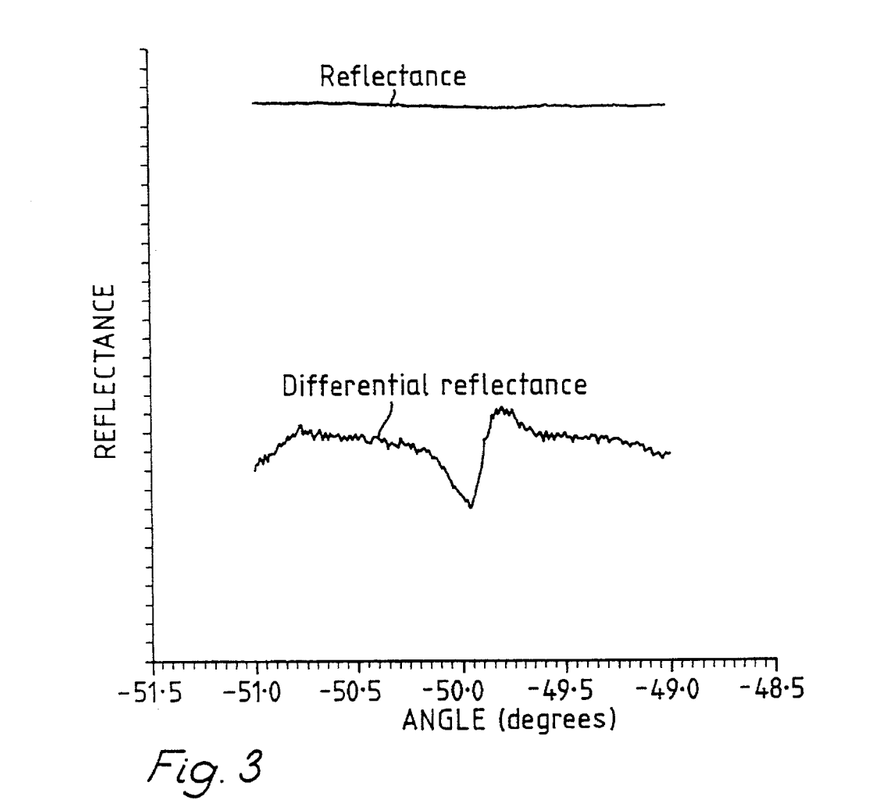
FIG. 3 shows the reflectance of a layer of silver on a high index glass prism.

The power of the differential measurement is shown in FIG. 3 for an angle modulating implementation. When the reflectance of a thick film of silver deposited on a high index glass prism was measured using a standard amplitude modulated detection system it appeared to be constant over the incident angle range as shown in waveform labeled "Differential Reflectance". However, modulating the incident angle with an acousto-optic deflector and with the lock-in amplifier set at very high gain (which accounts for the noise), the presence of a very weak surface plasmon resonance can be resolved from the differential reflectivity.

Figure 4:
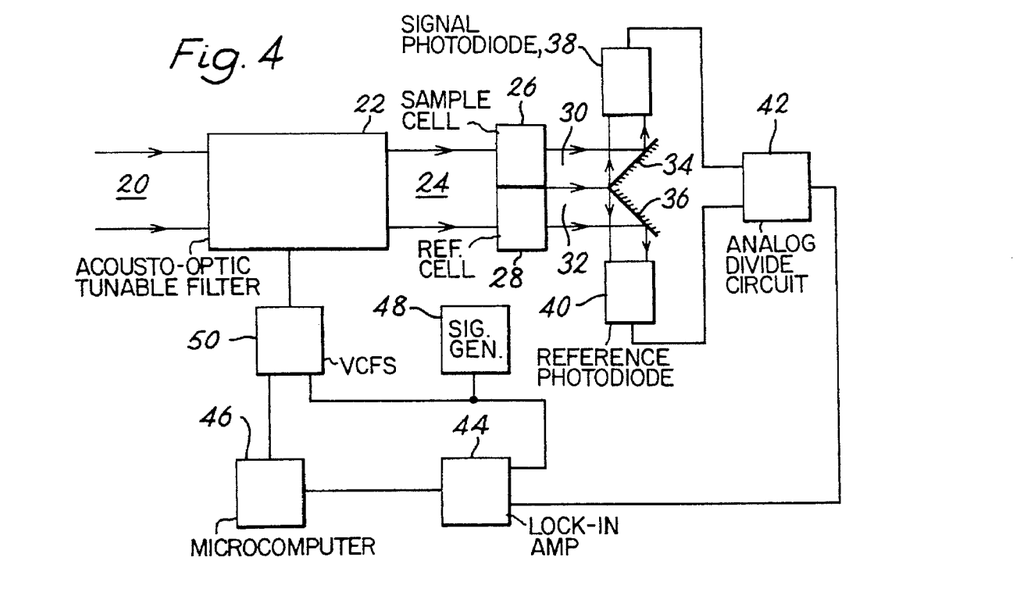
FIG. 4 illustrates schematically the measurement of differential transmission of a solution of potassium permanganate.

The invention also finds application in wavelength scanning implementations such as differential liquid spectroscopy measurement. Normally in a differential liquid spectrometer the absorption of a cell containing the solution of interest is compared with that of a pure water reference cell. The system illustrated in FIG. 4 has been used to measure the differential of this comparative absorption with respect to wavelength. A white light beam 20 is incident on an acousto-optic tunable filter 22. The filtered exit beam 24 passes to a sample cell 26 containing potassium permanganate and a reference cell 28 containing water to produce a probe beam 30 and a reference beam 32 which, after reflection by mirrors 34,36 are detected by respective signal and reference photodiodes 38,40. The outputs from these diodes 38, 40 are fed to an analogue divide circuit 42, lock-in amplifier 44 and microcomputer 46. A signal generator 48 provides a frequency modulation signal to the VCFS 50 and a reference signal for the lock-in amplifier 44. The microcomputer 46 provides an additional wavelength scanning signal to the VCFS 50 which drives the acousto-optic tunable filter 22.

Figure 5:
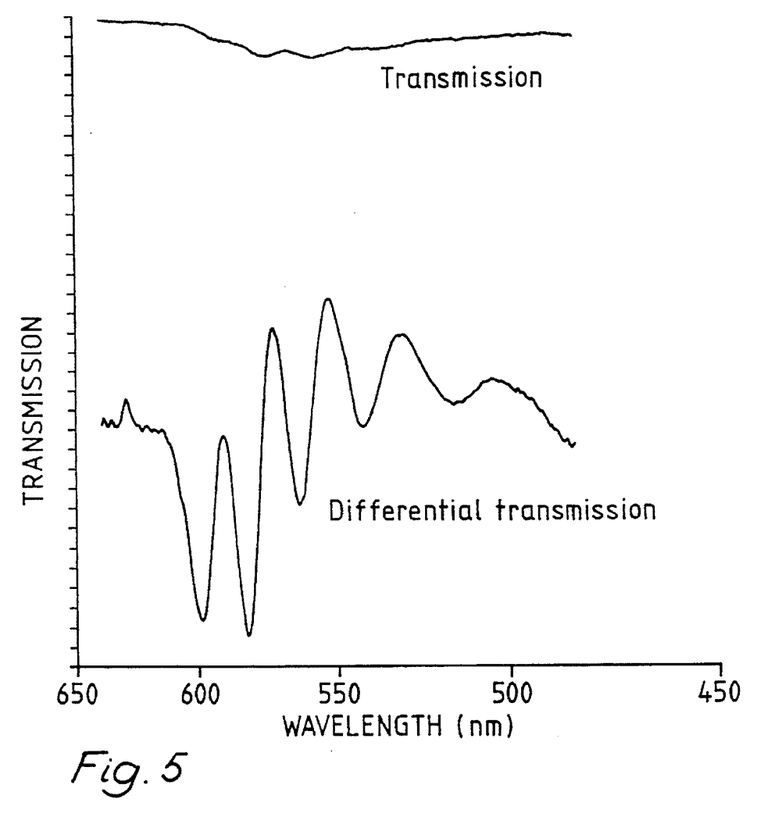
FIG. 5 is an indication of the optical transmission of a solution of potassium permanganate.

FIG. 5 shows how the differential of the transmission of a cell containing a very dilute solution of potassium permanganate strongly enhances the weak absorption features in the comparative signal.

Figure 6:
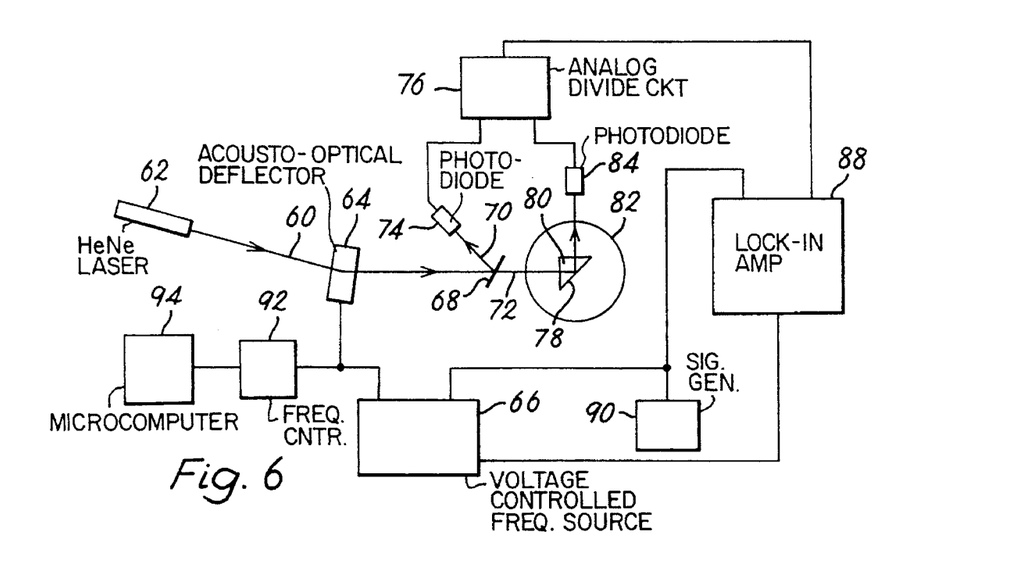
FIG. 6 is a schematic representation of apparatus used for measurement of small shifts in optical features.

A further embodiment of the invention allows the measurement of very small changes in the optical properties of the sample. This application requires the construction of the optical analogue of a phase locked loop. In practice this involves feeding back the output from the lock-in amplifier to a voltage controlled frequency source which drives the acousto-optic device as illustrated in FIG. 6. In this, a beam 60 of radiation from a HeNe laser 62 passes to an acousto-optical deflector 64 controlled by a frequency modulated drive signal from a voltage controlled frequency source (e.g.,a voltage controlled oscillator) 66. A partially reflecting mirror 68 splits the radiation into a reference beam 70 and a probe beam 72. The reference beam is detected by a photodiode 74 and passes to one input of an analog divide circuit 76. The probe beam 72 is reflected from a silvered layer on one surface 78 of a prism 80 mounted on a computer controlled rotating stage 82. It then passes to a photodiode 84 which is coupled to the other input of the analog divide circuit 76. A signal representative of the ratio of the signal to reference voltages passes from the divider circuit 76 to an input of a lock-in amplifier 88 which is also fed from the signal generator 90 which modulates the voltage-controlled frequency source 66. A feedback signal also passes from the lock-in amplifier 88 to the voltage-controlled frequency source 66. The output frequency of the voltage-controlled frequency source 66 is continuously measured by a frequency counter 92 and recorded by a microcomputer 94.

If the phase of the feedback is correctly adjusted it is possible for the system to lock on to the angle or wavelength at which a particular optical feature occurs.

For example, if the laser beam after deflection by the acousto-optic deflector 64 is incident on the silver layer shown in FIG. 1 at the angle for minimum reflectance, then the feedback signal from the lock-in amplifier 88 (set to the acousto-optic deflector modulation frequency) is zero. However if the surface plasmon angle shifts in response to a physical change in the sample then a large signal will be fed back from the amplifier lock-in amplifier 8 to the voltage-controlled frequency source 66. This signal will pull the center frequency of the voltage-controlled frequency source 66 and so the deflection angle of the laser beam to restore a null signal. In this way the incident angle is locked to the surface plasmon resonance and any shift in this angle will be measured as a shift in the center frequency of the voltage-controlled frequency source 66.

The fact that changes in the angle or wavelength of an optical feature are converted by the system to changes in frequency of the voltage-controlled frequency source results in a massive increase in sensitivity of the optical measurements. Typical drive frequencies for an acousto-optic deflector are 30–70 MHz and those for an acousto-optic tunable filter are 80–160 MHz and in principle these frequencies can be measured with a few Hertz accuracy giving a potential accuracy of 1 part in $10^7$. This is orders of magnitude more than can normally be achieved by direct measurement of angle or wavelength.

Figure 7:
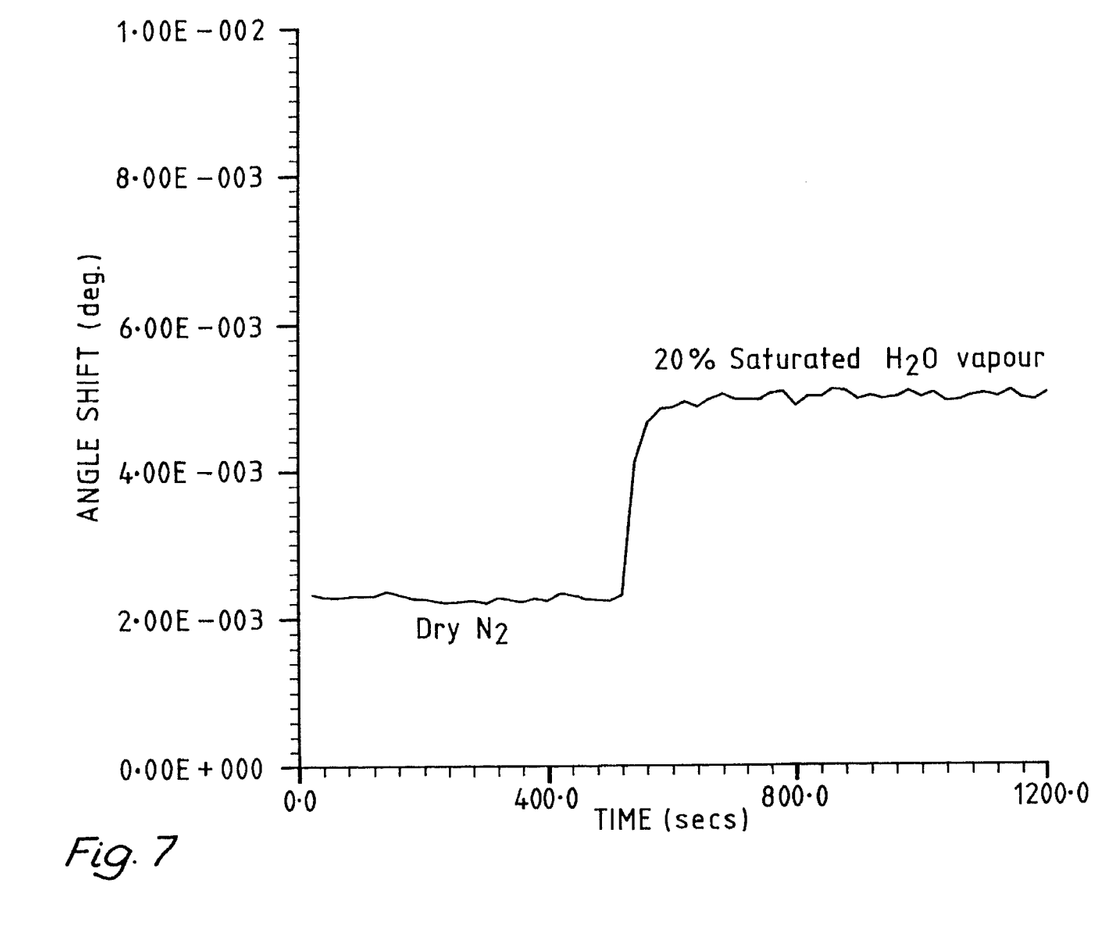
FIG. 7 shows the shift in plasmon angle due to water vapor condensing on a silver layer.

The technique has been demonstrated by sensing small shifts in the plasmon angle caused by unsaturated vapors condensing on to a silver layer. A typical result is shown in FIG. 7. In practice mechanical vibration, air currents and thermal drift have limited the sensitivity of the measurement to shifts of $10^{-4}$ degrees. However this is an improvement of two orders of magnitude over the the sensitivity previously obtained from this experiment. Also all of the noise generating factors can be reduced by careful device design. One possibility would be to integrate the acousto-optic device and sensor in a single crystal block.

Figure 8:
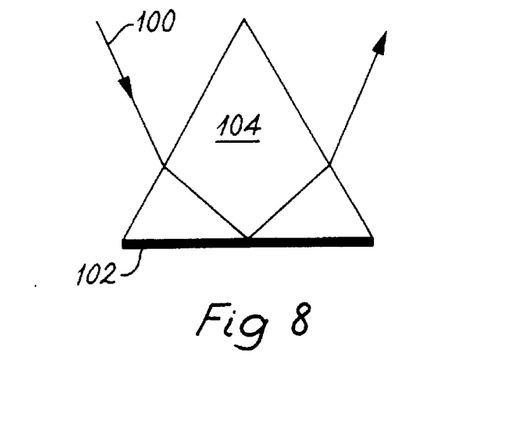
FIGS. 8–12 are explanatory diagrams.
Figure 9:
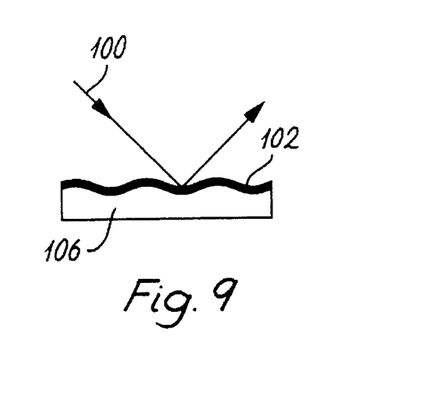
Figure 10:
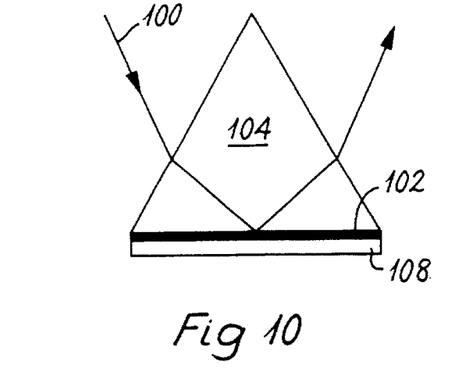
Figure 11:
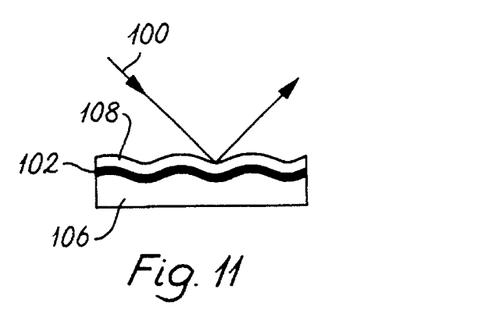
Figure 12:
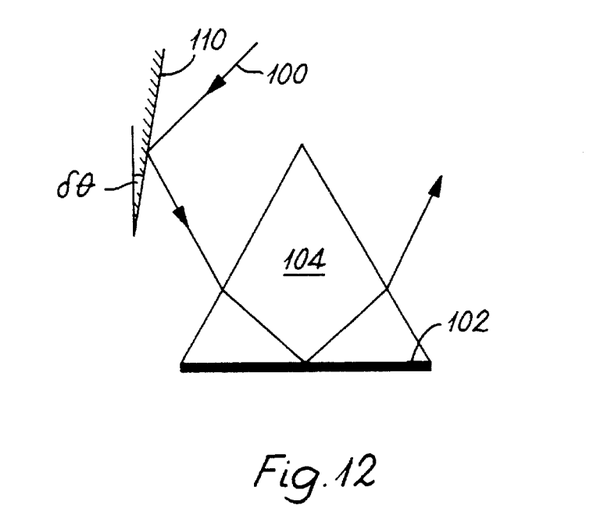

FIGS. 8 and 9 show embodiments used for detection of thin overlayers on metal surfaces. In these a beam of radiation 100 is reflected by a metal layer 102 on a surface of a prism 104 or grating 106. Alternatively, FIGS. 10 and 11 illustrate how an overlayer or waveguide of dielectric 108 can be added to the prism or grating of FIGS. 8 and 9. Small changes in the optical properties of the dielectric will then be measured with great accuracy. FIG. 12 shows a modification to the embodiment of FIG. 8 in which small changes dθ of the orientation of a mirror 110 in the path of the incident beam are measured.

Figure 13:
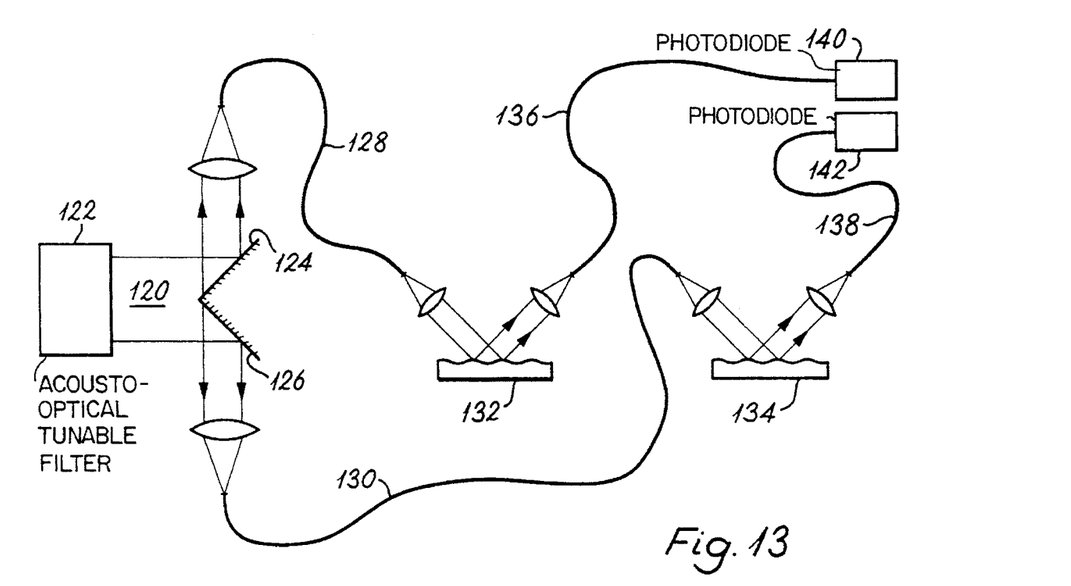
FIG. 13 is a schematic representation of apparatus incorporating optical fibers for remote measurement.

Referring to FIG. 13, which shows apparatus for remote measurement using optical fibers, a beam of filtered radiation 120 from an acousto-optical tunable filter 122 is split into two component beams by mirrors 124, 126. The component beams pass by way of optical fibers 128, 130 to respective probe and reference gratings 132, 134 and thence, by way of further fibers 136,138 to photodiodes 140,142 the output signals of which may be processed in the same manner as in the apparatus of FIG. 4.

Figure 14:
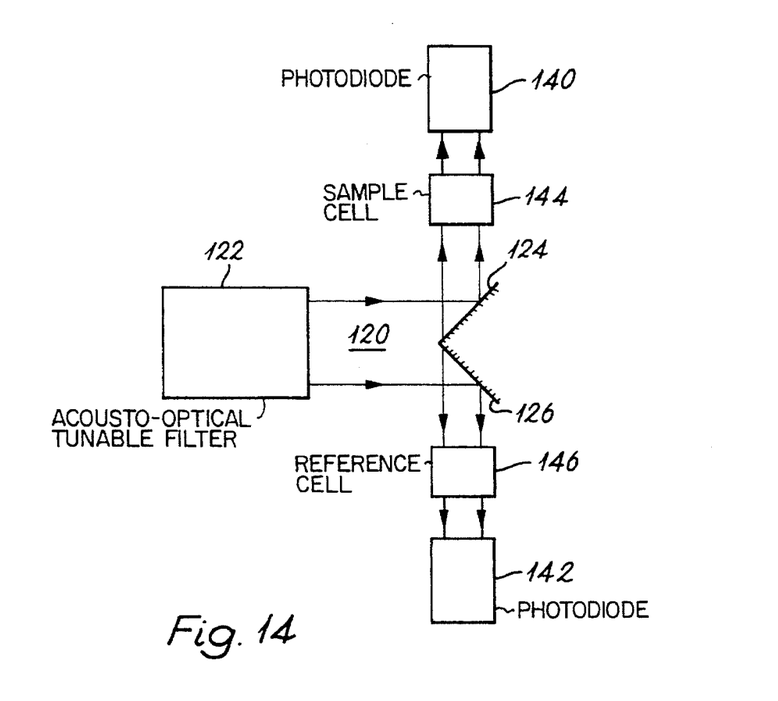
FIG. 14 is a diagrammatic representation of apparatus used for differential spectroscopy.

FIG. 14 shows an analogous apparatus used for differential spectroscopy using a sample cell 144 for a specimen under test and a reference cell 146 for a standard solution.

The invention may be applied to many optical measurement techniques. The possibilities include applications which make use of the differential with respect to the angle of incidence (photon momentum) and those which use the differential with respect to the wavelength (photon energy).

Specific differential applications include detection of thin overlayers ($<10^{-3}$ of a monolayer) on metal surfaces and detection of small changes of permittivity of an overlayer or waveguide and have applications in electrochemistry, gas sensing, biosensors, chromatography and pyroelectric infrared sensors.

Wavelength differential applications include measurements which can be made remotely at the end of fiber optic waveguides, spectroscopy, detecting weak features on strong backgrounds and locking on to optical signals of varying wavelength, possibly for surveillance purposes.

We claim:

1. Optical measuring apparatus for measuring an optical property of a sample under test, said optical measuring apparatus comprising:

an optical source providing a beam of optical radiation;

a signal generator providing a modulation signal at a modulation frequency;

an acousto-optical modulator receiving said modulation signal and said beam of optical radiation to provide a modulated beam by modulating a parameter of said beam of optical radiation at said modulation frequency, said acousto-optical modulator being an acousto-optical deflector which modulates an angle of deflection of said beam of optical radiation traversing said acousto-optical modulator;

photosensitive means for providing an electrical signal related to radiation incident thereto;

optical means for directing at least a portion of said modulated beam to said sample under test as a modulated probe beam, and to said photosensitive means so that said photosensitive means provides said electrical signal as a modulated electrical sample signal related to an optical property of said sample under test; and phase sensitive signal processing means, receiving said modulated electrical sample signal and said modulation signal, for deriving an output signal related to a differential of an optical property of said sample under test from said modulated electrical sample signal and said modulation signal.

2. Optical measuring apparatus according to claim 1, wherein:

said phase sensitive signal processing means is a lock-in amplifier.

3. Optical measuring apparatus for measuring an optical property of a sample under test, said optical measuring apparatus comprising:

an optical source providing a beam of optical radiation;

a signal generator;

a voltage controlled frequency source connected in series with said signal generator and providing a modulation signal;

an acousto-optical modulator connected in series with said signal generator and said voltage controlled frequency source, said acousto-optical modulator providing a modulated beam by modulating an angle of said beam of optical radiation at a frequency determined by said modulation signal;

beam splitter means for dividing said modulated beam into a modulated probe beam and a modulated reference beam, said modulated probe beam interacting with said sample under test;

first photosensitive means, receiving said modulated probe beam, for providing a first electrical signal related to said modulated probe beam;

second photosensitive means, receiving said modulated reference beam, for providing a second electrical signal related to said modulated reference beam;

first signal processing means, receiving said first electrical signal and said second electrical signal, for deriving a ratio signal representing a ratio of a property of said modulated probe beam and said modulated reference beam from said first electrical signal and said second electrical signal; and phase sensitive second signal processing means, receiving said ratio signal and said modulation signal, for deriving an output signal related to a differential of said optical property of said sample under test from said ratio signal and said modulation signal.

4. Optical measuring apparatus according to claim 3, wherein:
said phase sensitive second signal processing means is a lock-in amplifier.

5. Optical measuring apparatus according to claim 4, wherein:
said first signal processing means is an analog divide circuit.

6. Optical measuring apparatus according to claim 5, further comprising:
computer means for computing;
said second signal processing means supplying said output signal to said voltage controlled frequency source and to said computer means.

7. Optical measuring apparatus for measuring an optical property of a sample under test, said optical measuring apparatus comprising:
an optical source providing a beam of optical radiation;
a signal generator;
a voltage controlled frequency source connected in series with said signal generator and providing a modulation signal;
an acousto-optical modulator connected in series with said signal generator and said voltage controlled frequency source, said acousto-optical modulator providing a modulated beam by modulating a wavelength of said beam of optical radiation at a frequency determined by said modulation signal;
beam splitter means for dividing said modulated beam into a modulated probe beam and a modulated reference beam, said modulated probe beam interacting with said sample under test;
first photosensitive means, receiving said modulated probe beam, for providing a first electrical signal related to said modulated probe beam;
second photosensitive means, receiving said modulated reference beam, for providing a second electrical signal related to said modulated reference beam;
first signal processing means, receiving said first electrical signal and said second electrical signal, for deriving a ratio signal representing a ratio of a property of said modulated probe beam and said modulated reference beam from said first electrical signal and said second electrical signal;
phase sensitive second signal processing means, receiving said ratio signal and said modulation signal, for deriving an output signal related to a differential of said optical property of said sample under test from said ratio signal and said modulation signal; and
computer means for computing;
said phase sensitive second signal processing means supplying said output signal to said voltage controlled frequency source as a feedback signal and to said computer means.

8. Optical measuring apparatus according to claim 7, wherein:
said phase sensitive second signal processing means is a lock-in amplifier.

9. Optical measuring apparatus according to claim 8, wherein:
said first signal processing means is an analog divide circuit.

10. Optical measuring apparatus for measuring an optical property of a sample under test, said optical measuring apparatus comprising:
a laser providing a beam of optical radiation;
a signal generator;
a voltage controlled frequency source connected in series with said signal generator and providing a modulation signal;
an acousto-optical modulator connected in series with said signal generator and said voltage controlled frequency source, said acousto-optical modulator providing a modulated beam by modulating said beam of optical radiation at a frequency determined by said modulation signal, said acousto-optical modulator being an acousto-optical deflector which modulates an angle of deflection of said beam of optical radiation traversing said acousto-optical modulator;
beam splitter means for dividing said modulated beam into a modulated probe beam and a modulated reference beam, said modulated probe beam interacting with said sample under test;
a first photodetector, receiving said modulated probe beam and providing a first electrical signal related to said modulated probe beam;
a second photodetector, receiving said modulated reference beam and providing a second electrical signal related to said modulated reference beam;
an analog divide circuit, receiving said first electrical signal and said second electrical signal and deriving therefrom a ratio signal representing a ratio of a property of said modulated probe beam to said modulated reference beam;
a lock-in amplifier, receiving said ratio signal and said modulation signal and deriving therefrom an output signal related to a differential of said optical property of said sample under test.

11. Optical measuring apparatus for measuring an optical property of a sample under test, said optical measuring apparatus comprising:
a laser providing a beam of optical radiation;
a signal generator;
a voltage controlled frequency source connected in series with said signal generator and providing a modulation signal;
an acousto-optical modulator connected in series with said signal generator and said voltage controlled frequency source, said acousto-optical modulator providing a modulated beam by modulating said beam of optical radiation at a frequency determined by said modulation signal, said acousto-optical modulator being an acousto-optical tunable filter which modulates a wavelength of said beam of optical radiation;
beam splitter means for dividing said modulated beam into a modulated probe beam and a modulated reference beam, said modulated probe beam interacting with said sample under test;
a first photodetector, receiving said modulated probe beam and providing a first electrical signal related to said modulated probe beam;
a second photodetector, receiving said modulated reference beam and providing a second electrical signal related to said modulated reference beam;
an analog divide circuit, receiving said first electrical signal and said second electrical signal and deriving therefrom a ratio signal representing a ratio of a property of said modulated probe beam to said modulated reference beam;

a lock-in amplifier, receiving said ratio signal and said modulation signal and deriving therefrom an output signal related to a differential of said optical property of said sample under test.

12. A method of measuring an optical property of a sample under test comprising steps of:

providing a beam of optical radiation;

modulating a parameter of said beam of optical radiation at a modulation frequency in accordance with a modulation signal to provide a modulated beam;

directing at least a portion of said modulated beam to said sample under test as a modulated probe beam;

sensing a property of said modulated probe beam and providing an electrical sample signal related to said property of said modulated probe beam; and deriving, from said electrical sample signal and said modulation signal, a differential output signal of a reflectance of said sample under test.

13. A method of measuring an optical property of a sample under test according to claim 12, wherein:

said beam of optical radiation is modulated with respect to angle.

14. A method of measuring an optical property of a sample under test comprising steps of:

providing a beam of optical radiation;

modulating a parameter of said beam of optical radiation at a modulation frequency in accordance with a modulation signal to provide a modulated beam;

directing at least a portion of said modulated beam to said sample under test as a modulated probe beam;

sensing a property of said modulated probe beam and providing an electrical sample signal related to said property of said modulated probe beam; and deriving, from said electrical sample signal and said modulation signal, a differential output signal of an optical transmission of said sample under test.

15. A method of measuring an optical property of a sample under test according to claim 14, wherein:

said beam of optical radiation is modulated with respect to wavelength.

16. A method of measuring an optical property of a sample under test comprising steps of:

providing a beam of optical radiation;

modulating a parameter of said beam of optical radiation at a modulation frequency in accordance with a modulation signal to provide a modulated beam;

directing at least a portion of said modulated beam to said sample under test as a modulated probe beam;

sensing a property of said modulated probe beam and providing an electrical sample signal related to said property of said modulated probe beam; and deriving, from said electrical sample signal and said modulation signal, a differential output signal of a change in a plasmon angle of said sample under test.

17. A method of measuring an optical property of a sample under test according to claim 16, wherein:

said beam of optical radiation is modulated with respect to angle.

18. A method of measuring an optical property of a sample under test comprising steps of:

providing a beam of optical radiation;

modulating a parameter of said beam of optical radiation at a modulation frequency in accordance with a modulation signal to provide a modulated beam;

directing at least a portion of said modulated beam to said sample under test as a modulated probe beam;

sensing a property of said modulated probe beam and providing an electrical sample signal related to said property of said modulated probe beam; and deriving, from said electrical sample signal and said modulation signal, a differential output signal of a surface angle of said sample under test.

19. A method of measuring an optical property of a sample under test according to claim 18, wherein:

said beam of optical radiation is modulated with respect to angle.

20. Optical measuring apparatus for measuring an optical property of a sample under test, said optical measuring apparatus comprising:

an optical source providing a beam of optical radiation;

a signal generator providing a modulation signal at a modulation frequency;

an acousto-optical modulator receiving said modulation signal and said beam of optical radiation to provide a modulated beam by modulating a parameter of said beam of optical radiation at said modulation frequency, said acousto-optical modulator being an acousto-optical tunable filter which modulates a wavelength of said beam of optical radiation;

photosensitive means for providing an electrical signal related to radiation incident thereto;

optical means for directing at least a portion of said modulated beam to said sample under test as a modulated probe beam, and to said photosensitive means so that said photosensitive means provides said electrical signal as a modulated electrical sample signal related to an optical property of said sample under test; and phase sensitive signal processing means, receiving said modulated electrical sample signal and said modulation signal, for deriving a differential output signal of an optical property of said sample under test from said modulated electrical sample signal and said modulation signal.

21. Optical measuring apparatus according to claim 20, wherein:

said phase sensitive signal processing means is a lock-in amplifier.

* * * * *

UNITED STATES PATENT AND TRADEMARK OFFICE
CERTIFICATE OF CORRECTION

PATENT NO. : 5,583,643
DATED : December 10, 1996
INVENTOR(S) : GASS, et al

It is certified that error appears in the above-indentified patent and that said Letters Patent is hereby corrected as shown below:

On the title page, item [30], add -- Apr. 13, 1992 [WD] WIPO.......... PCT/GB92/00665 --

Signed and Sealed this

Twenty-ninth Day of April, 1997

Attest:

BRUCE LEHMAN

*Attesting Officer*     *Commissioner of Patents and Trademarks*